(12) United States Patent
Sawamura

(10) Patent No.: US 8,806,923 B2
(45) Date of Patent: Aug. 19, 2014

(54) SENSOR FOR DETECTING MATERIAL TO BE TESTED

(75) Inventor: Makoto Sawamura, Ibaraki (JP)

(73) Assignee: National Institute for Materials Science, Tsukuba-shi (JP)

( * ) Notice: Subject to any disclaimer, the term of this patent is extended or adjusted under 35 U.S.C. 154(b) by 300 days.

(21) Appl. No.: 13/259,437

(22) PCT Filed: Mar. 26, 2010

(86) PCT No.: PCT/JP2010/055467
§ 371 (c)(1),
(2), (4) Date: Feb. 24, 2012

(87) PCT Pub. No.: WO2010/110458
PCT Pub. Date: Sep. 30, 2010

(65) Prior Publication Data
US 2012/0137797 A1    Jun. 7, 2012

(30) Foreign Application Priority Data

Mar. 26, 2009    (JP) .................................. 2009-077715

(51) Int. Cl.
*G01N 37/00* (2006.01)

(52) U.S. Cl.
USPC ........................................................ 73/61.61

(58) Field of Classification Search
None
See application file for complete search history.

(56) References Cited

U.S. PATENT DOCUMENTS 6,464,940 B1    10/2002 Akioka et al.

FOREIGN PATENT DOCUMENTS

| JP | 2000-356619 A | 12/2000 |
| JP | 2004-108815 A | 4/2004 |
| JP | 2004-347532 A | 12/2004 |
| JP | 2005-218310 A | 8/2005 |
| JP | 2008-116210 A | 5/2008 |
| JP | 2008-134255 A | 6/2008 |
| WO | 2008/035697 A1 | 3/2008 |

OTHER PUBLICATIONS

International Search Report of PCT/JP2010/055467, mailing date Jun. 22, 2010. Previously submitted.

*Primary Examiner* — Robert R Raevis
(74) *Attorney, Agent, or Firm* — Westerman, Hattori, Daniels & Adrian, LLP

(57) ABSTRACT

A sensor for detecting material to be tested 100 having small variations in electrochemical measurement values includes a work electrode 1 and a counter electrode 2 integrated into one via an insulator 3. As a result of contact between the material to be tested and the work electrode 1, output voltage changes. The work electrode 1 smaller than the counter electrode 2 and the insulator 3 is installed on a part of the surface of the insulator 3, and a peripheral wall 4 for surrounding the work electrode 1 is formed on the insulator 3 to operate as a storage part.

12 Claims, 13 Drawing Sheets

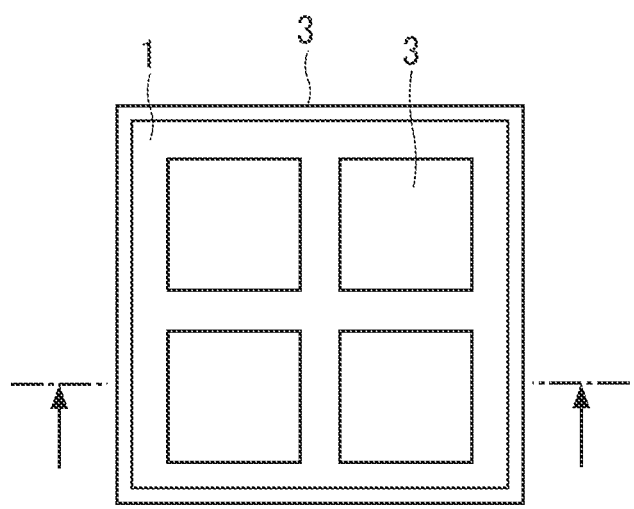
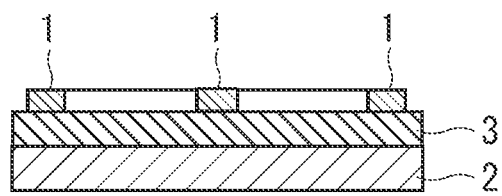

SENSOR FOR DETECTING MATERIAL TO BE TESTED

TECHNICAL FIELD

The present invention relates to a sensor including a counter electrode, and a work electrode integrated with the counter electrode via an insulator, for detecting a material to be tested based on a change in output voltage by making the material such as biologically active agent contact the work electrode, and more specifically a sensor for detecting material to be tested quickly with a small amount of specimen material.

BACKGROUND ART

A sensor for detecting proteins or trace ingredients of physiologically active substances in organisms has a signal conversion element, namely a transducer, in addition to a molecular recognition element. The molecular recognition element detects chemical or physical reactions, and the signal conversion element converts detected signals into electrical signals to detect materials to be tested.

As one of such sensors, the one using a field-effect transistor (FET) as a signal conversion element is known, and a pH sensor, glucose sensor, etc. using an ion-sensitive field-effect transistor having an ion-selective membrane have been put to practical use. By using an FET as a signal conversion element, downsizing and integration of sensors can be achieved based on conventional semiconductor manufacturing technologies.

It has recently been desired to achieve a sensor that operates more quickly, simply, and sensitively compared to conventional reagents for antibody test, reagents for antigen test such as viruses, and equipment for the tests. For example, as disclosed in Patent Literatures 1 and 2, some biosensors using an FET as a signal conversion element have been proposed. Furthermore, sensors using a two-terminal element as a signal conversion element have also been proposed (Patent Literature 3).

The inventor et al. have proposed in Patent Literature 4 a sensor in simple and highly-flexible structure including a two-terminal signal conversion element and having high sensitivity comparable to that of the sensor integrating an FET as a signal conversion element.

However, only a few such sensors have been put to practical use as pH sensors or glucose sensors equipped with a signal conversion element. In other words, a sensor equipped with a molecular recognition element and a signal conversion element for detecting proteins or trace ingredients of biologically active substances in organisms has yet to be put to practical use.

CITATION LIST

Patent Literature

Patent Literature 1: JP2005-218310A
Patent Literature 2: JP2004-347532A
Patent Literature 3: JP2004-108815A
Patent Literature 4: JP2008-116210A

SUMMARY OF THE INVENTION

Technical Problem

It is an object of the invention to provide a sensor for detecting material to be tested with small variability in electrochemical measurement.

Solution to Problem

To achieve the above objective, a sensor of the first embodiment of the present invention includes: a work electrode; and a counter electrode integrated with the work electrode via an insulator, wherein output voltage varies with the contact of the material with the work electrode, characterized in that the work electrode is formed smaller than the counter electrode and the insulator and is provided to a part of the surface of the insulator, and that a peripheral wall for surrounding the work electrode is formed on the insulator so as to function as a storage part for accommodating the material to be tested.

More specifically, in the sensor for detecting a material to be tested having the work electrode and the counter electrode integrated with the work electrode via the insulator, wherein the output voltage varies with the contact of the material with the work electrode, the counter electrode is formed in a shape of a plate, the insulator covers the upper face of the counter electrode, the work electrode is provided on a part of the surface of the insulator, a peripheral wall for surrounding the work electrode is formed on the insulator, the contact area between the work electrode and the insulator is smaller than the contact area between the counter electrode and the insulator, and a power is connected to the work electrode and the counter electrode.

In the first embodiment, the peripheral wall may be formed on the work electrode. Specifically, the sensor having the work electrode and the counter electrode integrated into one via the insulator, wherein the output voltage changes as a result of contact between the material to be tested and the work electrode, is characterized in that it has a wall formed on the work electrode, the wall has an opening for holding the material to be tested, the work electrode has openings for exposing the surface of the insulator, and the material held within the opening of the wall contacts the insulator through the openings of the work electrode.

A sensor of the present invention in the second embodiment is characterized in that a reference electrode is provided in addition to the work electrode of the sensor in the first embodiment.

A sensor of the present invention in the third embodiment is characterized in that the reference electrode of the sensor in the second embodiment is placed on the outside of the storage part.

A sensor of the present invention in the fourth embodiment is characterized in that the reference electrode of the sensor in the second embodiment is embedded in the peripheral wall forming the storage part.

A sensor of the present invention in the fifth embodiment is characterized in that the reference electrode of the sensor in the second embodiment is placed within the storage part.

A sensor of the present invention in the sixth embodiment is characterized in that a plurality of work electrodes are provided in any one of the sensors in the first to the fifth embodiments, and that the storage part is provided to each of the work electrodes.

A sensor of the present invention in the seventh embodiment is characterized in that a plurality of work electrodes are placed within one storage part in any one of the sensors in the first to the sixth embodiments.

A sensor of the present invention in the eighth embodiment is characterized in that the storage part of any one of the sensors in the first to the seventh embodiments stores a given amount of material to ensure stable operation of the work electrode.

A sensor of the present invention in the ninth embodiment is characterized in that the peripheral wall forming the storage part in any one of the sensors in the first to the eighth embodiments is made to have water repellency.

A sensor of the present invention in the tenth embodiment is characterized in that the peripheral wall forming the storage part in any one of the sensors in the first to the eighth embodiments is made to have oil repellency.

Advantageous Effect of the Invention

According to the present invention, since the change in output voltage can be detected more accurately than conventional sensors, stable electrochemical measurement data of materials to be tested can be obtained.

This opens new possibilities of this sensor, namely the difference of materials, which has been conventionally unanalyzable, is expected to become analyzable electrochemically.

Furthermore, with the sensors in the second to the fifth embodiments, a reference electrode is provided so as to function as a grounding wire for reference, namely as a reference electrode whose potential does not change. Consequently, even if the potential should deviate as a result of attachment of molecules to each of the work electrode and the reference electrode, the reference electrode presents the reference, allowing true potential of the work electrode to be determined. Namely, by providing the reference electrode, the potential of both electrodes can be determined stably.

In addition, this reference electrode is also effective in a case where a constant potential is given to the work electrode to observe the change in antigen-antibody reactions with time, and the antigen starts reacting with the antibody on the surface of the work electrode, thus changing the electrical field on the surface of the work electrode.

As shown in the sensor in the fourth embodiment, of the sensors in the second to the fifth embodiments, by embedding the reference electrode within the peripheral wall constituting the storage part, contamination of the reference electrode can be prevented without fail.

Furthermore, as shown in the sensor in the sixth embodiment, by providing each of the plurality of work electrodes with a storage part, a number of samples can be processed simultaneously, which is another advantage in addition to the advantages described above.

As shown in the sensor in the seventh embodiment, by providing a plurality of work electrodes in a storage part, average value of the materials to be tested can be detected even if the materials to be tested are stored unevenly within the storage part. In addition, some of the work electrodes can be made to operate as reference electrodes, and in that case, there is no need to provide reference electrodes in addition to the work electrodes. Furthermore, with the sensor in the ninth embodiment, hydrophilic materials to be tested do not climb on the peripheral wall, and with the sensor in the tenth embodiment, lipophilic materials to be tested do not climb on the peripheral wall. Consequently, leakage from the storage part can be prevented. The smaller the capacity of the storage part, the more valuable this leakage prevention effect becomes.

BRIEF DESCRIPTION OF THE DRAWINGS

FIG. 11 (*a*) is a plan view of a work electrode or reference electrode in a shape of a lattice, and (*b*) is a longitudinal cross-sectional view of the electrode along the line shown in (*a*).

DESCRIPTION OF EMBODIMENTS

The present invention will hereinafter be described in detail by referring to the attached drawings.

Figure 1A:
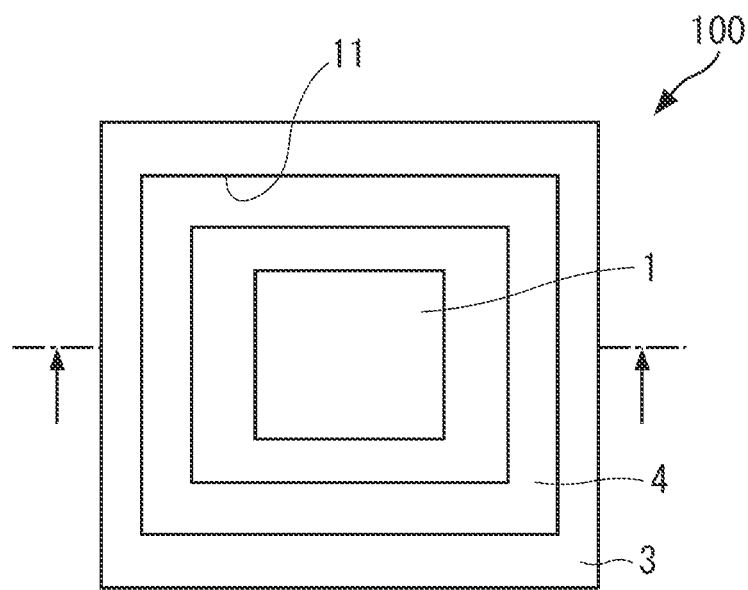
FIG. 1 (*a*) is a plan view of a single-cell sensor having a work electrode in a storage part in accordance with the embodiment of the present invention, and (*b*) is a longitudinal cross-sectional view of the sensor along the line shown in (*a*).
Figure 1B:
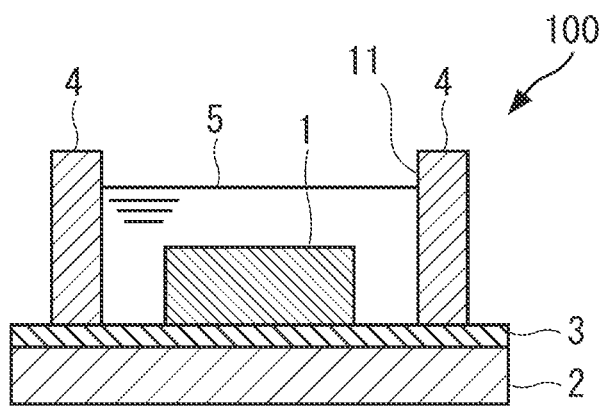
Figure 2:
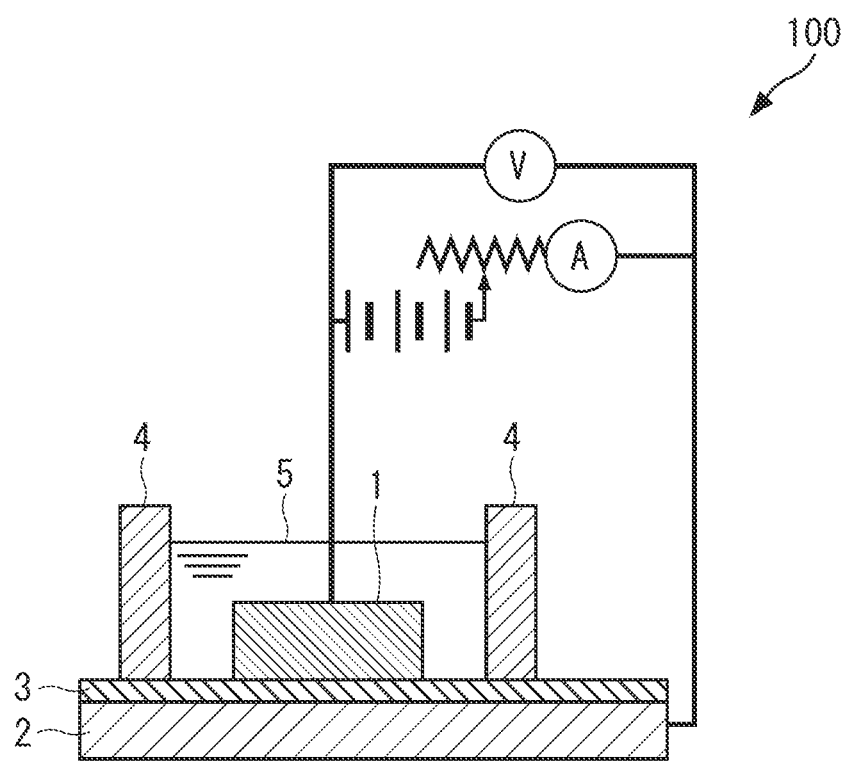
FIG. 2 is a typical connection diagram of the single-cell sensor shown in FIG. 1, with an ammeter and voltmeter connected to it.

FIG. 1 (a) is a plan view of a sensor 100 in accordance with the first embodiment of the present invention, and FIG. 1 (b) is its cross-sectional view. FIG. 2 is a typical connection diagram of the single-cell sensor 100 shown in FIG. 1, with an ammeter and voltmeter connected to it.

The sensor 100 includes a work electrode 1, a counter electrode 2, insulator 3, and a peripheral wall 4. The item including the above may hereinafter be called the sensor main unit.

The counter electrode 2 is made of a material having the function of semiconductor or conductor and is formed in a shape of a plate to ensure independent shape retaining property, which is effective for self-retaining the shape of the entire sensor. As semiconductors, IV-group elements such as silicon and germanium, III-V compounds such as gallium arsenide and indium phosphide, and II-VI compounds such as zinc telluride are known. As conductive substances, aluminum, nickel, etc. are known. All of those can be used in the same way as the examples shown below. It is preferable that the plate thickness fall within the 0.1 mm to 1.0 mm range, more preferably within the 0.3 mm to 0.5 mm range. The counter electrode 2 in this embodiment is made of a silicon substrate.

The insulator 3 is a member for insulating the work electrode 1 from the counter electrode 2. As the insulator 3, inorganic compounds such as silicon oxide, silicon nitride, aluminum oxide, and titanium oxide, and organic compounds such as acrylic resins and polyimide are known. Inorganic substances can be deposited as an insulator on the surface of the counter electrode 2 in a form of a thin film by the deposition method, etc., whereas organic insulating film can be attached to the surface of the counter electrode 2 for integration.

On the surface of the insulator 3, a functional group such as hydroxyl group, amino group, and carboxyl may be introduced.

To immobilize an antibody, etc. on the surface of the insulating film, by bonding the functional group to the surface in advance, the antibody is made to bond with these functional groups. This achieves more stable immobilization, and allows antibodies to be orientated.

It is desirable that the thickness of the insulator 3 fall within the 10 nm to 1000 nm range, more preferably within the 20 nm to 500 nm range. If the insulator 3 is too thin, tunnel current may be fed, and if the insulator 3 is too thick, sensitivity may degrade.

In this embodiment, as shown in FIG. 1 (b), the insulator 3 having approximately the same area as the counter electrode 2 is formed, covering the entire top surface of the counter electrode.

The work electrode 1 for applying power to the counter electrode 2 is integrated with the counter electrode 2 via the insulator 3. With the sensor 100 in accordance with this embodiment, the work electrode 1 is formed in a shape unsymmetrical to the counter electrode 2. Furthermore, the material of the work electrode 1 is different from that of the counter electrode 2. Specifically, the work electrode 1 is made to be smaller than the top face of the counter electrode 2 and the insulator 3 covering the top face of the counter electrode 2. This allows the surface of the insulator 3 to be exposed partially. The contact surface area between the work electrode 1 and the insulator 3 is made to be smaller than the contact surface between the counter electrode 2 and the insulator 3. As materials for work electrode 1, metals such as gold, platinum, titanium, and aluminum are used preferably, but conductive plastic, etc. can also be used.

It is preferable that the shape of the work electrode 1 allow the contact area with the sample solution to become large with respect to the unit volume of the sample solution, in order for the work electrode 1 to become susceptible to the effect of dielectric constant, etc. of the sample solution so that sensitive detection of the concentration of material to be tested is ensured.

In addition, to increase the contact area of the sample solution per unit volume, the work electrode 1 is made to have a number of openings, for example. Examples of the shape of work electrodes having a number of openings include the shape of a blind shown in FIG. 9, concentric circles, or shape of a donut, shown in FIG. 10, and the shape of a lattice shown in FIG. 11.

Figure 9A:
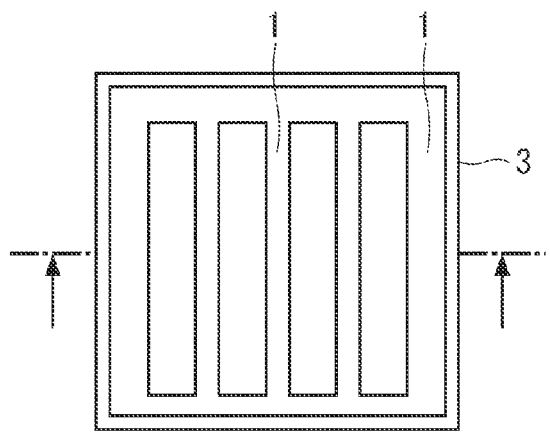
FIG. 9 (*a*) is a plan view of a work electrode or reference electrode in a shape of a blind, and (*b*) is a longitudinal cross-sectional view of the electrode along the line shown in (*a*).
Figure 9B:
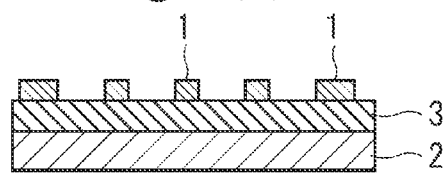
Figure 10A:
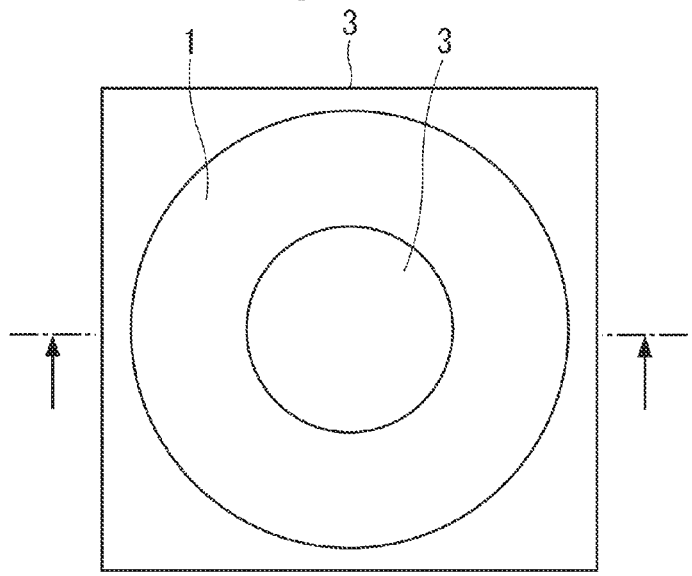
FIG. 10 (*a*) is a plan view of a work electrode or reference electrode in a shape of a donut, and (*b*) is a longitudinal cross-sectional view of the electrode along the line shown in (*a*).
Figure 10B:
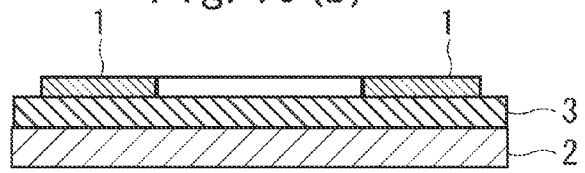

In the case of the metallic work electrode in the shape of a blind shown in FIG. 9, the width of each slat of the metal preferably falls within the range as thin as from 10 μm to several hundred μm. If the width of the slats is as thin as shown above, the area of the openings of the electrode can be increased, and a number of recognition molecules to be tested can be bonded to the insulating film in the region of the openings as required. Meanwhile, if the width of the slats is less than 10 μm, the value of the current fed from the work electrode to the sample solution in a state of a thin film decreases, and consequently the effect as the electrode is hardly exhibited. The reason for this is assumed to be as follows: As a result of the change in the electric field under the work electrode from a "planar" to a "linear" structure, the electric lines of force perpendicular to the silicon substrate or insulating film disperse radially under the work electrode, thus preventing sufficiently high electric field from being obtained.

With the metallic work electrode in the shape of a blind, the interval between work electrodes, namely the interval between slats, preferably falls within the 100 μm to 200 μm range, in order for as many recognition molecules to be bonded to the insulating film in the region of the relevant openings, and to provide a sufficiently wide reaction field.

To obtain a large effective contact area of the work electrode per unit volume of the sample solution, the height of the work electrode preferably falls within the range from 0.1 μm to several hundred μm.

The sensor 100 in this embodiment is equipped with a peripheral wall 4 surrounding the whole or a part of the work electrode 1. The peripheral wall 4 is formed on the surface of the insulator 3. This peripheral wall 4 and the insulator 3 together form a storage part 11, which serves as a reservoir for containing a sample solution.

It is desirable that the surface of the peripheral wall have the property opposite to that of the material to be tested. If the material to be tested is hydrophilic, the surface of the peripheral wall is preferably made to be water-repellent. If the material to be tested is lipophilic, the surface of the peripheral wall is preferably made to be oil-repellent. Possible outflow of material to be tested in a liquid form into the storage part 11 over the peripheral wall can thus be prevented. As materials of such peripheral wall, water-repellent resins such as photoresist AZ5214E manufactured by Clariant Japan and polyimide resins such as PIQ, or fluorine-series resins typified by Teflon™ can be used as required. It is also possible to use such resins not as a constituent material but as a material for coating the surface of the peripheral wall.

It is desirable that the depth of the material to be tested stored in the storage part 11 be as uniform as possible, in order to obtain stable data. It is therefore preferable that the surface of the insulator 3, which serves as the bottom of the storage part 11, be made to be as flat as possible, and that the height of the peripheral wall 4 be made to be as uniform as possible.

The holding capacity of the storage part 11 is determined based on the electrical characteristics of the material to be tested, but it is desirable when detecting biomaterials such as those shown in the following examples that the capacity fall within the 0.001 µL to 25 µL range, more preferably, within the 0.1 µL to 2.0 µL range.

The height of the peripheral wall is set to be higher than that of the work electrode 1 to cover the top face of the work electrode with the stored material to be tested. Specifically, the height preferably falls within the 1 µm to 2 mm range, more preferably within the 2 µm to 10 µm range.

The space surrounded by the peripheral wall and the insulating film becomes storage part 11, where a sample solution of a given amount can be stored. When the peripheral wall is made of a water-repellant material, a sample solution, an aqueous solution in general, may rise from the storage part 11, but does not flow out of the storage part in general.

The shape of the storage part 11 in a plan view has no restrictions, but from the viewpoint of ease of manufacturing, squares (including rectangles), or circular shapes (including ellipses), are desirable. The length of a side of the square, or the diameter of the circular shape, preferably falls within the 2 mm to 4 mm range, considering the required amount of sample solution.

Figure 3:
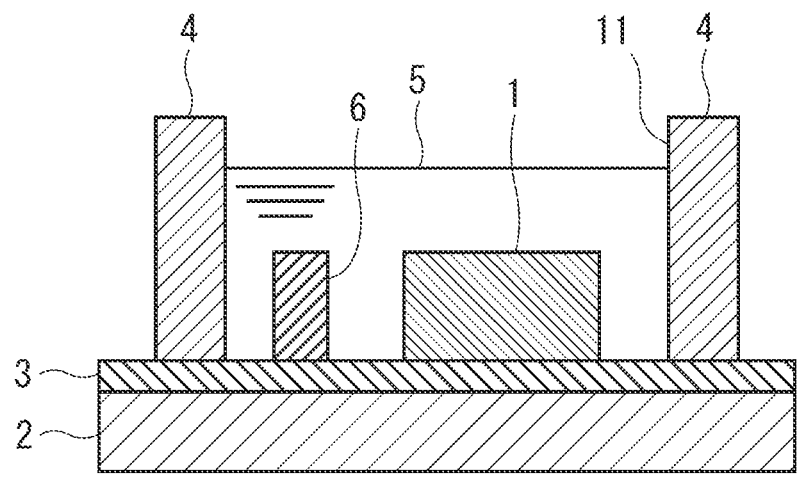
FIG. 3 is a longitudinal cross-sectional view of a single-cell sensor equipped with a reference electrode in a storage part, in addition to the work electrode, in accordance with the embodiment of the present invention.
Figure 4:
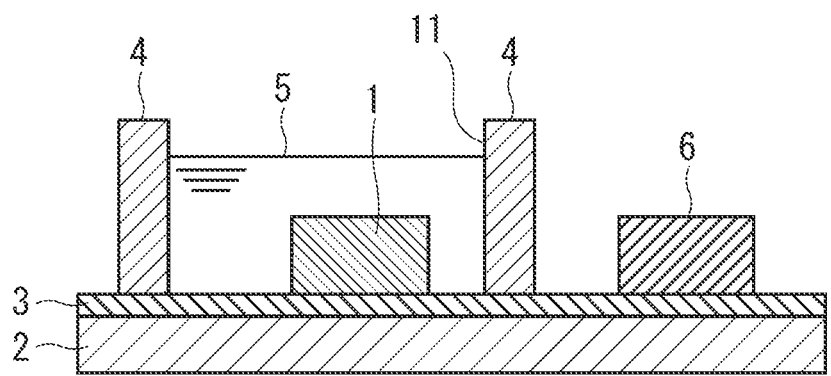
FIG. 4 is a longitudinal cross-sectional view of a single-cell sensor equipped with a reference electrode outside of a storage part in accordance with the embodiment of the present invention.
Figure 5:
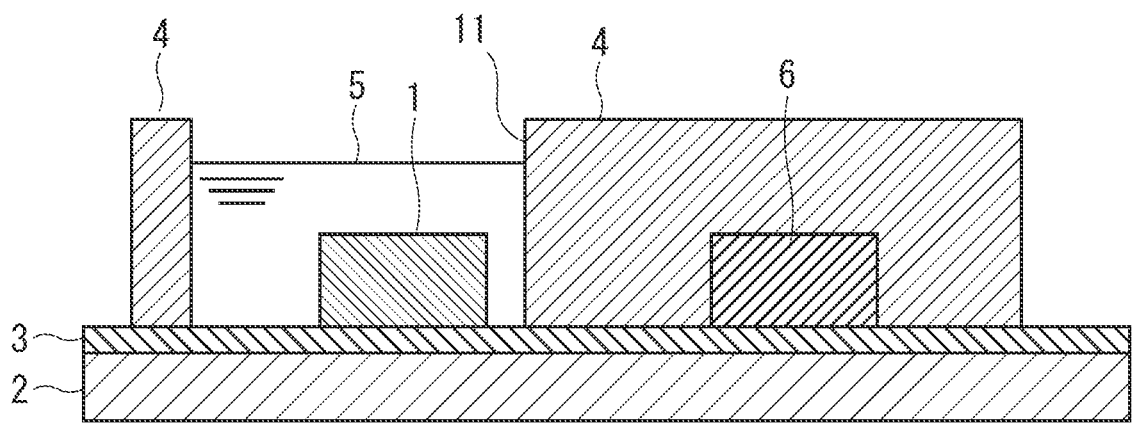
FIG. 5 is a longitudinal cross-sectional view of a single-cell sensor equipped with a reference electrode embedded in a peripheral wall in accordance with the embodiment of the present invention.
Figure 6:
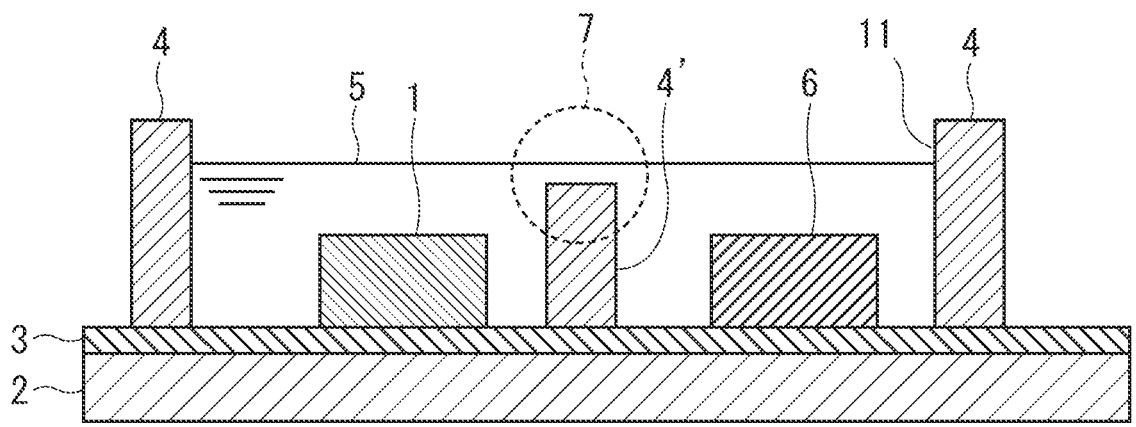
FIG. 6 is a longitudinal cross-sectional view of a single-cell sensor equipped with a work electrode and a reference electrode in a storage part, with the work electrode and the reference electrode separated from each other with a salt bridge, in accordance with the embodiment of the present invention.
Figure 7:
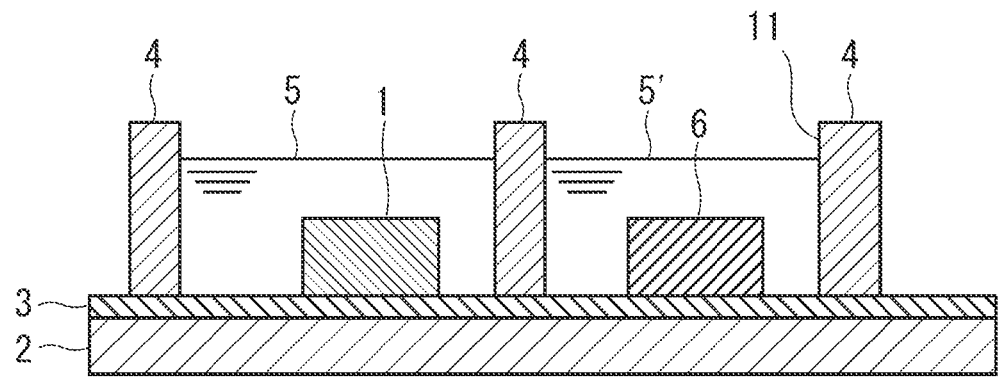
FIG. 7 is a longitudinal cross-sectional view of a single-cell sensor equipped with a work electrode and a reference electrode in a storage part, with the work electrode and the reference electrode separated from each other completely with a peripheral wall.
Figure 8:
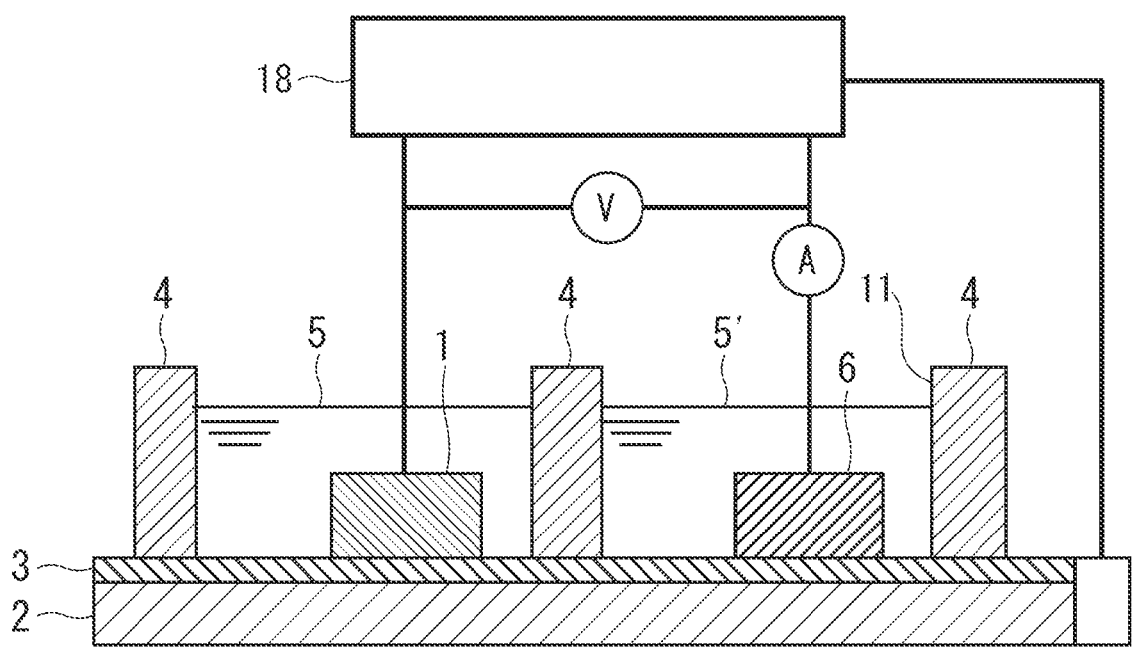
FIG. 8 is a typical connection diagram of the single-cell sensor shown in FIG. 7, with an ammeter and voltmeter connected to it.

The sensor 100 according to the present invention may have a reference electrode 6, in addition to the work electrode 1, on the insulating film as required. The reference electrode 6 may be provided within the storage part 11 as shown in FIG. 3, or outside the storage part 11 as shown in FIG. 4. The reference electrode 6 may also be embedded in the peripheral wall 4 as shown in FIG. 5. As shown in FIG. 6, the work electrode 1 and the reference electrode 6 may be installed within the storage part 11, and the work electrode 1 and the reference electrode 6 may be separated from each other by a peripheral wall 4' capable of forming a salt bridge 7. As shown in FIG. 7, the work electrode 1 and the reference electrode 6 may be installed within the storage part 11, and the work electrode 1 and the reference electrode 6 may be separated from each other completely with the peripheral wall 4. FIG. 8 is a typical connection diagram of the main unit of the single-cell sensor shown in FIG. 7, with an ammeter and a voltmeter connected to it. The member shown as 18 in FIG. 8 is a potentiostat.

Figure 12:
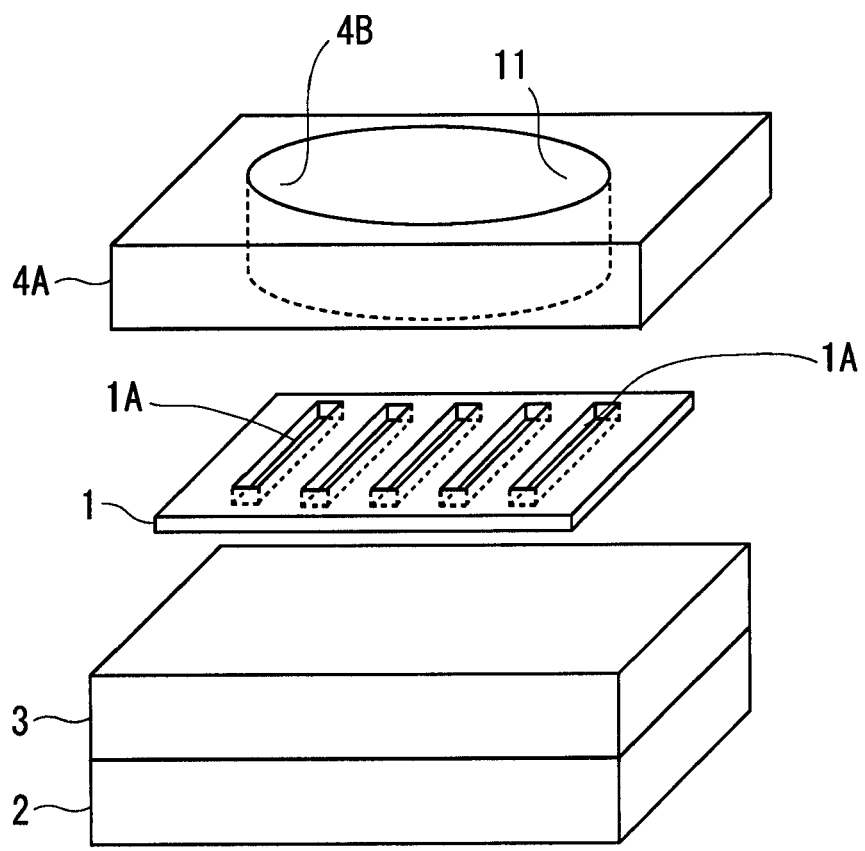
FIG. 12 is an illustrative diagram showing the structure of a sensor including a substrate, an insulating film, an electrode, and a peripheral wall made of photoresist.

The sensor 100 according to the present invention can be manufactured by electron beam lithography, photolithography, etc. The insulator 3 is formed on the surface of the counter electrode 2 in a substrate form made of silicon, etc., namely on a silicon substrate, and on the surface of this insulator 3, the work electrode 1 and/or reference electrode 6 (metal) in a desired patterns are/is formed. Around the work electrode 1 and/or the reference electrode 6, the peripheral wall 4 in a desired pattern is formed to define the storage part 11. FIG. 12 presents a typical configuration of the counter electrode 2, insulator 3, work electrode 1, and peripheral wall 4 made of photoresist. The counter electrode 2, insulator 3, work electrode 1, and peripheral wall 4 are actually closely contacted to each other.

In the sensor 100 shown in FIGS. 1 to 11, the peripheral wall 4 in a desired pattern is formed around the work electrode 1, but the configuration shown in FIG. 12 may be selected. In the configuration shown in FIG. 12, the peripheral wall is formed on the work electrode 1. This peripheral wall, which is made of the same material as that of the peripheral wall 4 described above, will hereinafter be called a wall member 4A because the layout is different. This wall member 4A has an opening 4B for holding a sample. In the region of the work electrode 1 to be laid under this opening 4B, openings 1A for exposing the surface of the insulator 3 are formed. Consequently, the sample solution held within the opening 4B of the wall member 4A is made to contact the surface of the insulator 3 via the openings 1A of the work electrode 1. The shape and the number of the openings 1A to be formed on the work electrode 1 are not limited to the shape and the number shown in FIG. 12, but a shape of a blind shown in FIG. 9, concentric circles, or a shape of a donut, shown in FIG. 10, or a shape of a lattice shown in FIG. 11 may be adopted.

The wall member 4A formed on the work electrode 1 and the peripheral wall 4 formed around the work electrode 1 may also be formed in a C-shape in planer view, with a part of the wall cut off, in addition to the shape covering the entire opening.

Using the sensor 100 thus obtained, a package 110 (FIG. 13) including the main unit of the single-cell sensor, a unit 120 (FIG. 14) with a socket 14 attached to the package 110, and furthermore a single-cell sensor apparatus for detecting material to be tested 130 (FIG. 15) with an enclosure 15 provided to the unit 120 and a detachable transparent cover 16, for example, attached to the enclosure, can be assembled.

Figure 13:
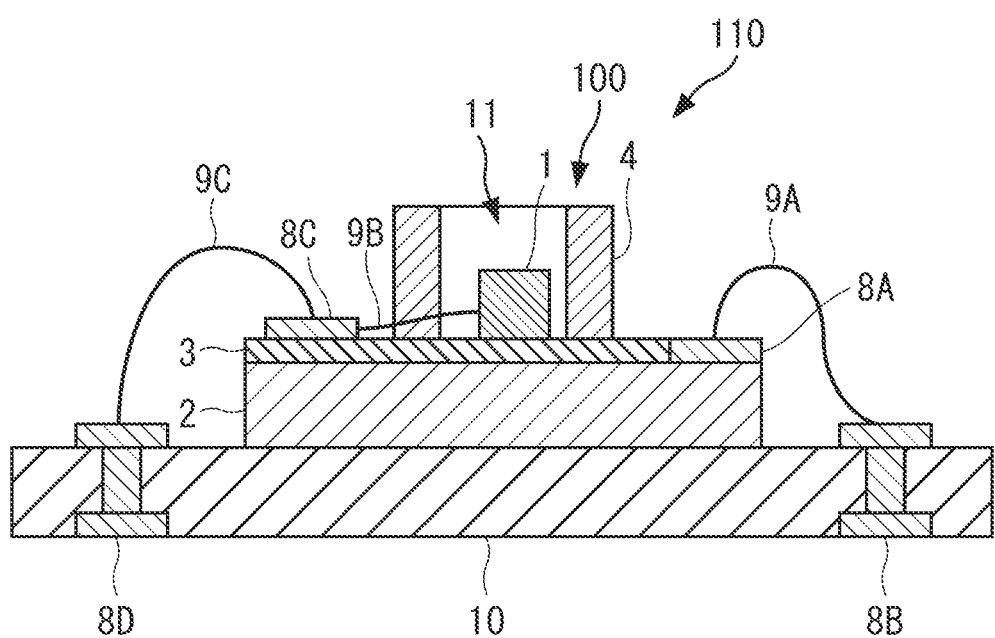
FIG. 13 is a longitudinal cross-sectional view of a package containing a single-cell sensor in accordance with the embodiment of the present invention.

Specifically, in the package 110 shown in FIG. 13, a counter electrode 2 is placed on a glass epoxy substrate 10. On this counter electrode 2, an electrode pad 8A and an insulator 3 are formed. The electrode pad 8A is connected to electrode pad 8B using a bonding wire 9A. The electrode pad 8B is mounted, penetrating the glass epoxy substrate 10. On the insulator 3, a work electrode 1 and a peripheral wall 4 for surrounding the work electrode are formed. The work electrode 1 is connected to an electrode pad 8C formed on the insulator 3 using a bonding wire 9B. The electrode pad 8C is connected to an electrode pad 8D, which is mounted, penetrating the glass epoxy substrate 10, using a bonding wire 9C.

Figure 14:
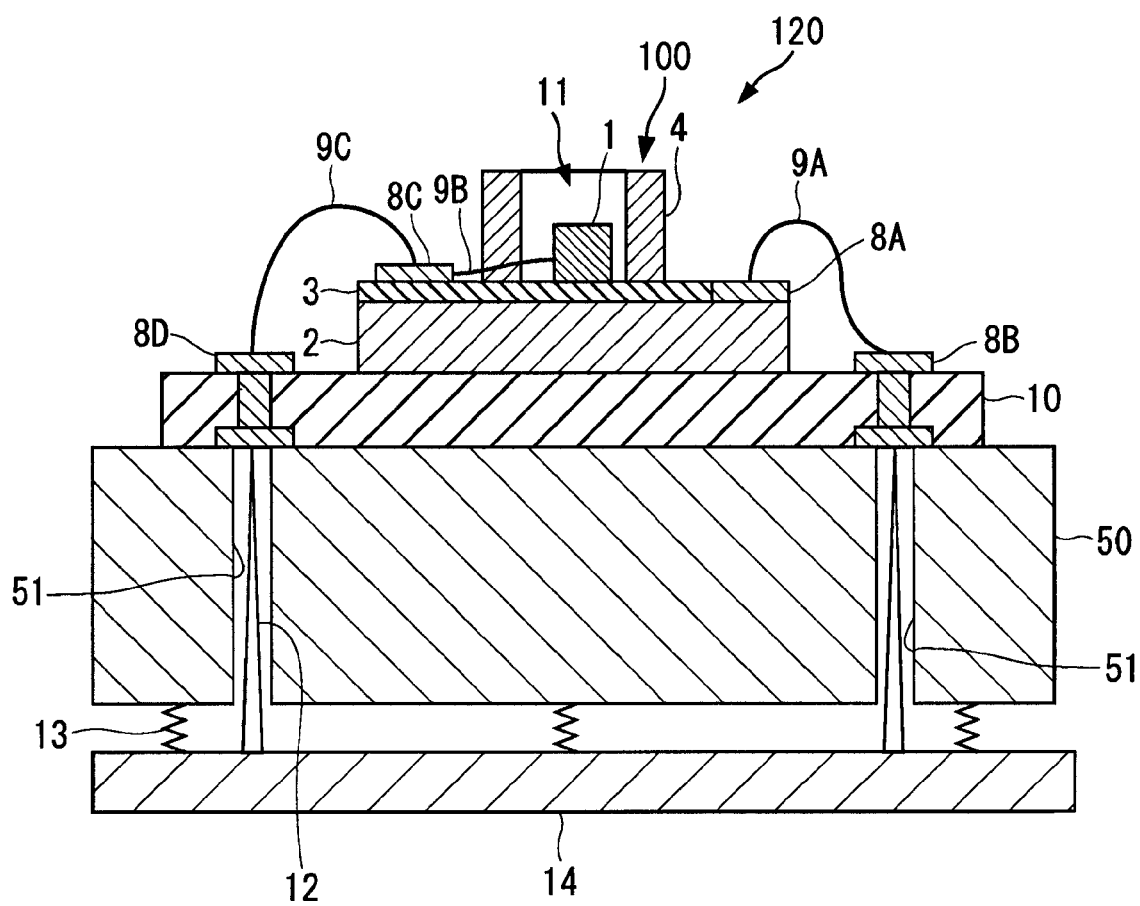
FIG. 14 is a longitudinal cross-sectional view of a single-cell sensor unit contained in the package shown in FIG. 13, to which a socket is attached.
Figure 15:
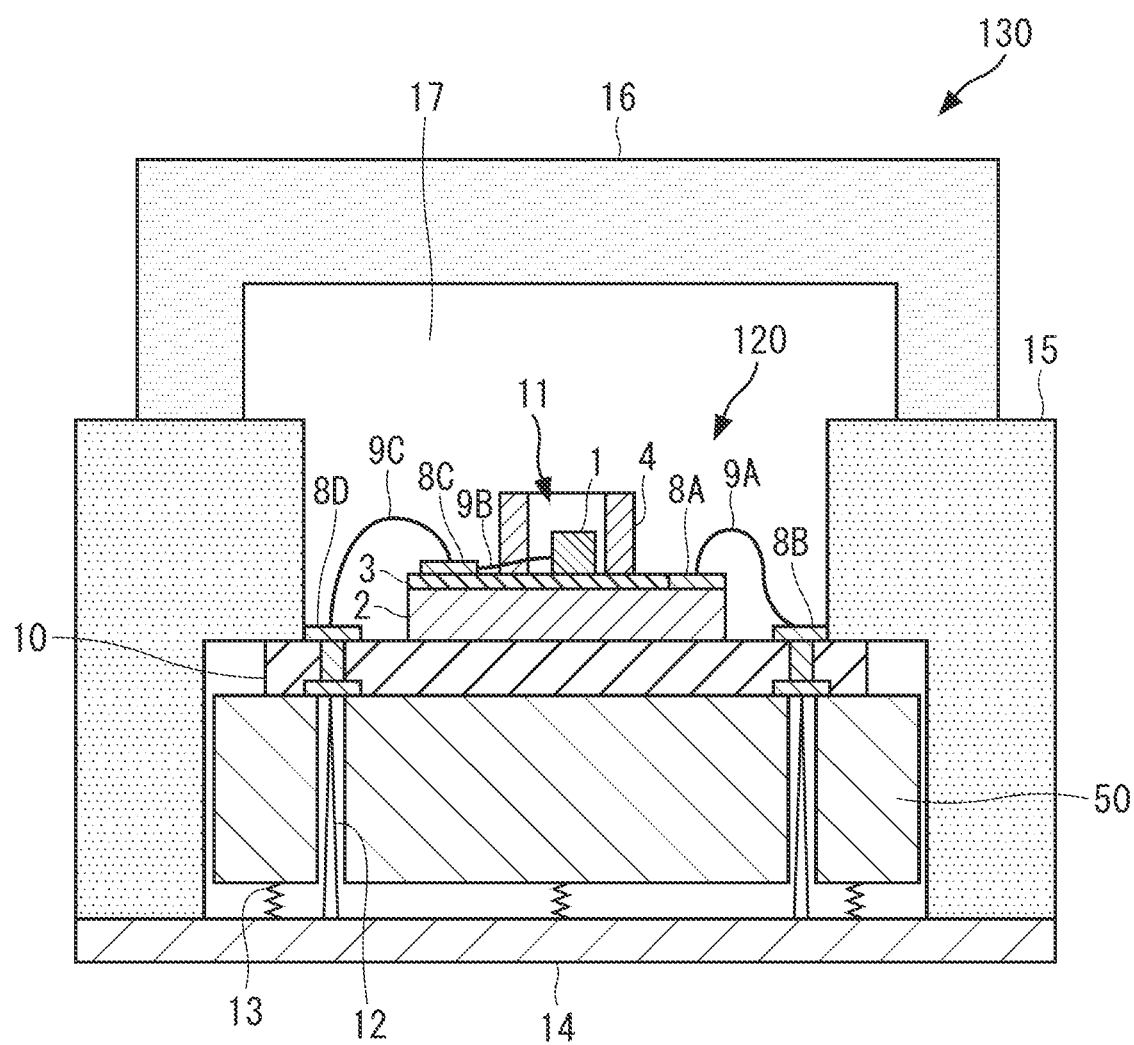
FIG. 15 is a drawing illustrating the single-cell sensor apparatus with enclosure provided to the package and the socket shown in FIG. 14, and a detachable cover set to the enclosure.

In the unit 120 shown in FIG. 14, the package 110 shown in FIG. 13 is fixed on the top surface of a fixed base 50. The fixed base 50 is provided with holes 51 penetrating the fixed base at positions corresponding to the electrode pads 8B, 8D. A base 14 is mounted at the bottom of the fixed base 50 via springs 13. The springs 13 are mounted for the purpose of separating the fixed base 50 from the base 14. From the top face of the base 14, pin-shaped electrodes 12 are protruding upward. These pin-shaped electrodes 12 are inserted into the holes 51 of the fixed base, and if the fixed base 50 is pressed down toward the base against the force of the springs 13, the pin-shaped electrodes 12 contacts the electrode pads 8B, 8D. This allows the power from a power supply (not shown) to be supplied to the sensor 100 via the electrode pads 8B, 8D.

In the sensor 100 related to the embodiment of the present invention described above, most of the electric lines of force from the work electrode 1 enter the counter electrode 2 made of a silicon substrate via the insulator 3, namely an insulating film. The leak electric field of the work electrode contributes to detection.

Figure 17:
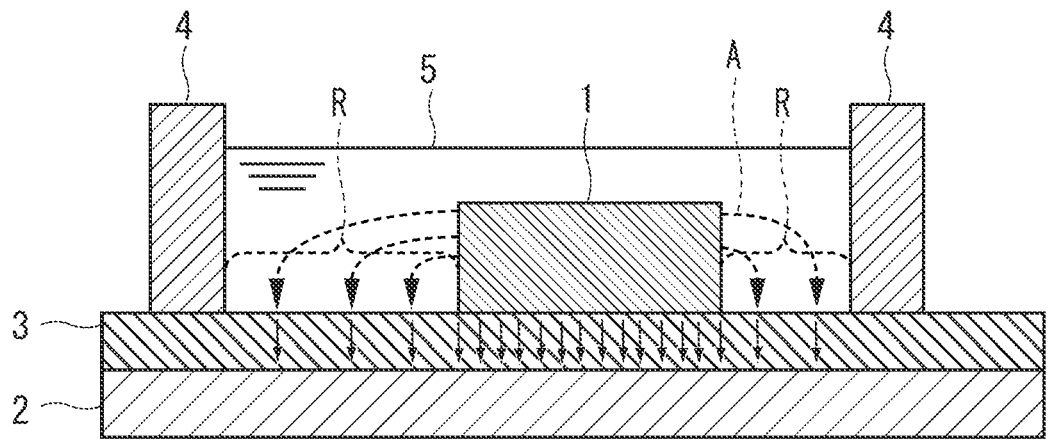
FIG. 17 is a drawing illustrating the reaction field of a sensor in accordance with the embodiment of the present invention.
Figure 18:
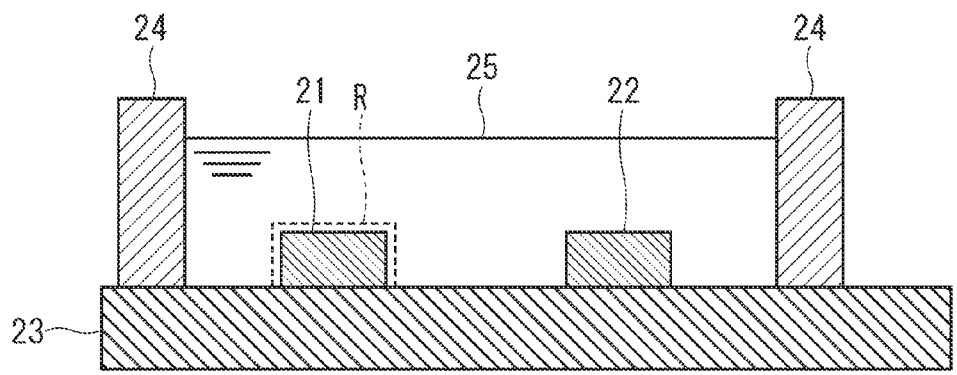
FIG. 18 is a drawing illustrating the reaction field of a conventional sensor having a two-terminal signal conversion element.

FIG. 17 is a drawing illustrating the reaction field R of the sensor 100 in accordance with the embodiment of the present invention. As shown in FIG. 18, the reaction field R of a conventional sensor having two-terminal signal conversion element exists only on the work electrode. In the sensor 100 in accordance with the present invention, the reaction field R spreads widely so that most of the electric lines of force A coming from the side of the work electrode contacting the material to be tested enter the counter electrode 2 through the insulator 3 around the work electrode 1. According to the sensor 100, a uniform electric field can be produced in a wide and flat region of the insulating film around the work electrode 1.

This makes it possible for the sensor 100 to obtain voltage for similar materials to be tested highly accurately, unlike conventional apparatuses, and thus stable electrochemical measurement data can be obtained.

Figure 16:
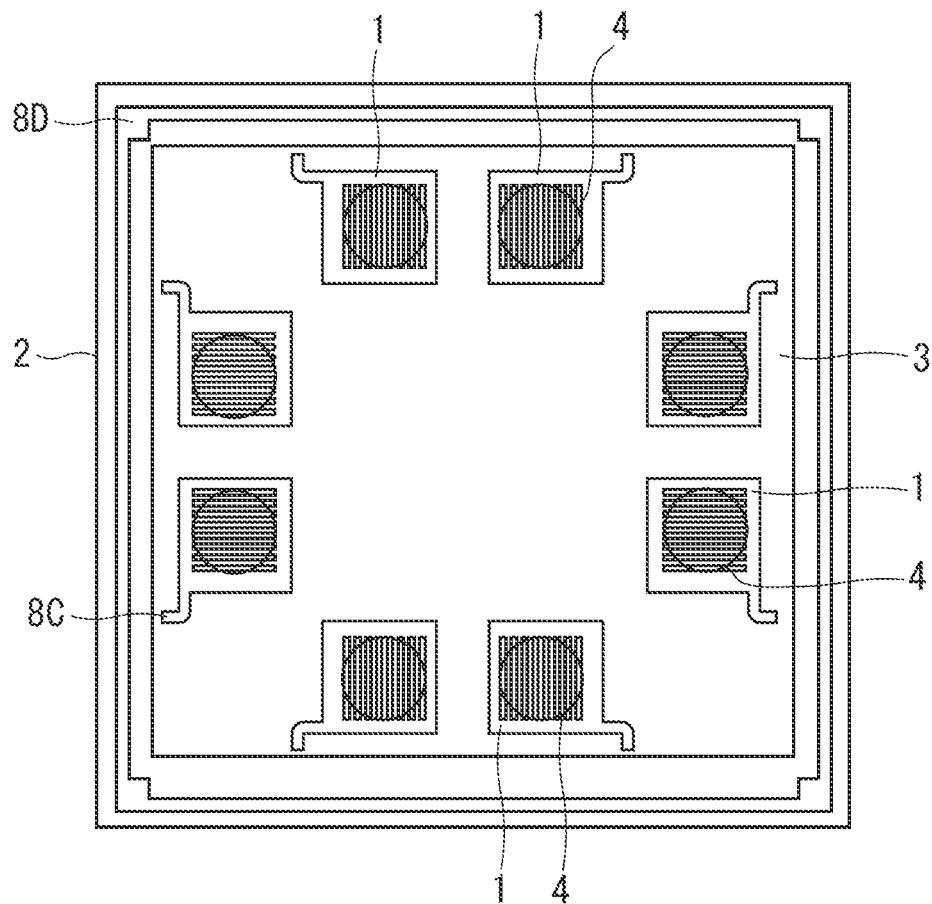
FIG. 16 is a plan view of a multi-cell sensor having eight cells in accordance with the embodiment of the present invention.

In the above description, the number of work electrode 1 disposed on the counter electrode 2 was assumed to be one. However, the umber of work electrodes can be two or more. FIG. 16 illustrates a multi-cell sensor, wherein a plurality of work electrodes 1 and storage part 11 provided for each of the work electrodes 1 are placed on a counter electrode 2. As an example, a multi-cell sensor for detecting material to be tested 100 having eight cells is shown. In this case, it is preferable that work electrodes be electrically separated from each other using p-n junction, etc. to allow each of them to send detection data independently.

8-cell sensor not provided with a storage part 11 (T0020, Comparative example 1) was created.

The operation characteristics of the sensor (T0005) of the present invention and the operation characteristics of the sensor for comparison (T0020) were examined. Each sensor chip was connected according to FIG. 2 to examine the operation characteristics. As an AC power supply, a function generator was used, and oscilloscope was used instead of an ammeter.

A constant amount, 1 μL for example, of ultrapure water, phosphate buffered saline (PBS), and blood serum were dropped on the reaction field of each sensor using a micropipet, and the maximum output voltage values were compared. Using a function generator, sinusoidal waves having voltage of 50 mV and frequency of 100 Hz were input, and the output voltage was measured using the oscilloscope. The output voltage of the oscilloscope was displayed in the average value of 16 cycles, and the maximum value was obtained in the automatic measurement mode. The minimum unit of voltage was 4 mV. Table 1 summarizes the obtained data. As the function generator, function generator SG-4104 by Iwatsu Test Instruments Corporation was used, and as the oscilloscope, digital oscilloscope DS-5102 by Iwatsu Test Instruments Corporation was used.

TABLE 1

Comparison of output voltage between the sensor of the present invention and the sensor for comparison
(Unit: mV)

| Electrode No. | Before dropping of sample | | After dropping of ultrapure water | | After dropping of PBS | | After dropping of blood serum | |
|---|---|---|---|---|---|---|---|---|
| | Example 1 | Comparative example 1 | Example 1 | Comparative example 1 | Example 1 | Comparative example 1 | Example 1 | Comparative example 1 |
| 1 | 136 | 136 | 192 | 192 | 192 | 204 | 192 | 196 |
| 2 | 136 | 136 | 192 | 192 | 192 | 192 | 192 | 192 |
| 3 | 136 | 136 | 192 | 192 | 192 | 196 | 192 | 192 |
| 4 | 136 | 136 | 192 | 196 | 192 | 188 | 188 | 196 |
| 5 | 136 | 136 | 188 | 196 | 192 | 196 | 188 | 204 |
| 6 | 136 | 136 | 188 | 196 | 188 | 204 | 188 | 196 |
| 7 | 136 | 136 | 192 | 192 | 192 | 188 | 188 | 192 |
| 8 | 136 | 136 | 192 | 192 | 192 | 196 | 192 | 192 |
| Average value | 136 | 136 | 191 | 193.5 | 191.5 | 195.5 | 190 | 195 |
| S.D. | 0 | 0 | 1.7 | 1.9 | 1.3 | 5.8 | 2 | 3.9 |

To the insulator 3 within the storage part of the sensor 100 of the present invention, recognition molecules to be tested such as antibody or enzyme can be attached in advance as the heterogeneous method. Or, these recognition molecules to be tested can be used for solution reaction, without allowing them to be attached, as the homogeneous method. By attaching the tested material recognition molecules to be tested, specific proteins and chemical substances can be detected specifically, and thus the apparatus can be used as a biosensor.

Example 1

The integrated 8-cell sensor (T0005, Example 1) shown in FIG. 16 was created. As the counter electrode 2, a silicon substrate, on one face of which a 0.3-μm-thick $SiO_2$ film, namely insulator 3, was formed, was used. The length of the side of the square silicon substrate was 15 mm, and its thickness was 550 μM. As the work electrode 1, a metal electrode in a shape of a blind (FIG. 12) having thickness of 0.77 μm was used, and as the peripheral wall 4 for forming the storage part, a photoresist (AZ5214E, Clariant Japan) was used. The photoresist was 2 μm thick, and the diameter of the storage part was 2 mm. As a comparative example, an integrated Before the sample was added, both sensors exhibited standard deviation of 0.0 mV, exhibiting the uniformity of reaction field. When ultrapure water was dropped, no significant difference in voltage was found between both sensors, but when PBS and blood serum were dropped, a significant difference in voltage was found between both sensors. When blood serum was added, the standard deviation of Comparative Example 1 was 3.9 mV, whereas that of Example 1 was 2 mV, which was approximately half of the variability of Comparative Example 1. In the case of PBS, the standard deviation of Comparative Example 1 was 5.8 mV, whereas that of Example 1 was 1.3 mV, which is approximately ¼ of the variability of Comparative Example 1.

One of the causes of significant difference in variability of output voltage is as follows: When a storage part 11 is provided, the area where the sample contacts the reaction field at the cell bottom remains constant, whereas, the area where the sample contacts the reaction field does not remain constant when the storage part 11 is not provided. Meanwhile, in the case of ultrapure water, since the solution did not expand because of its high surface tension, the area contacting the reaction field remained constant, and consequently the variability of output voltage of both sensors was assumed to be small. The average value of output voltage of the sensor for comparison having no storage part was found to be higher than that of Example 1 by 2.5 mV in the case of ultrapure water, by 4 mV in the case of PBS, and by 5 mV in the case of blood serum. In the case of the sensor for comparison, a systematic error is considered to be included, in addition to the magnitude of standard deviation.

In Example 2 to be described later, PBS was used as a solvent. In Comparative Example 1, which does not have cells, since the standard deviation obtained when PBS was used was 5.8 mV, which far exceeds the minimum scale on the chart, namely, 2 mV, (FIG. 19), it is difficult to use it for high-sensitivity detection of antigen-antibody reactions.

Example 2

Homogeneous Method, AC Measurement

As the sensor shown in Example 1, an integrated 8-cell sensor was used, and detection and measurement of a specific protein, α-fetoprotein (AFP), were conducted by the homogeneous method and AC measurement.

(1) Five μL each of an anti-α-fetoprotein (AFP) antibody solution diluted with PBS to concentration of 100 ng/mL was poured into four test tubes. Test tubes containing antibody were thus prepared.

(2) Into four test tubes, 5 μL each of PBS not containing AFP was poured. Test tubes not containing antibody were thus prepared.

(3) An AFP solution of 5 μL diluted with PBS to concentrations of 0.0, 1.6, 6.25, and 25 ng/mL was dropped into each series of test tubes described above, namely test tubes containing antibody and test tubes not containing antibody, and mixed. As a result, the test tubes containing the following eight types of reaction liquids were obtained.

Sample A: AFP antibody (100 ng/mL) 5 μL+AFP antigen (0 ng/mL) (PBS) 5 μL

Sample B: AFP antibody (100 ng/mL) 5 μL+AFP antigen (1.6 ng/mL) 5 μL

Sample C: AFP antibody (100 ng/mL) 5 μL+AFP antigen (6.25 ng/mL) 5 μL

Sample D: AFP antibody (100 ng/mL) 5 μL+AFP antigen (25 ng/mL) 5 μL

Sample E: PBS 5 μL+AFP antigen (0 ng/mL) (PBS) 5 μL

Sample F: PBS 5 μL+AFP antigen (1.6 ng/mL) 5 μL

Sample G: PBS 5 μL+AFP antigen (6.25 ng/mL) 5 μL

Sample H: PBS 5 μL+AFP antigen (25 ng/mL) 5 μL (4) The above test tubes were sealed tightly, and stored overnight at room temperature.

(5) The above eight types of reaction liquids of 0.85 μL each were dropped into eight cells on a chip.

(6) Sinusoidal voltage having amplitude of 10 V and frequency of 20 Hz was applied between the electrodes, and output voltage of cells having different concentrations was measured continuously.

(7) Similar experiments were conducted using three other integrated 8-cell sensors, and the average output voltage was found.

Table 2 lists the average values of the maximum output voltage specific to antigen concentrations in both cases where antibody existed and did not exist.

TABLE 2

| Sample | Antibody | Antigen concentration (mg/mL) | Average value of maximum output voltage (mV) |
| --- | --- | --- | --- |
| A | With | 0.0 | 892.0 |
| B | With | 1.6 | 883.5 |
| C | With | 6.25 | 883.0 |
| D | With | 25.0 | 875.0 |
| E | Without | 0.0 | 878.5 |
| F | Without | 1.6 | 878.5 |
| G | Without | 6.25 | 884.5 |
| H | Without | 25.0 | 885.0 |

Figure 19:
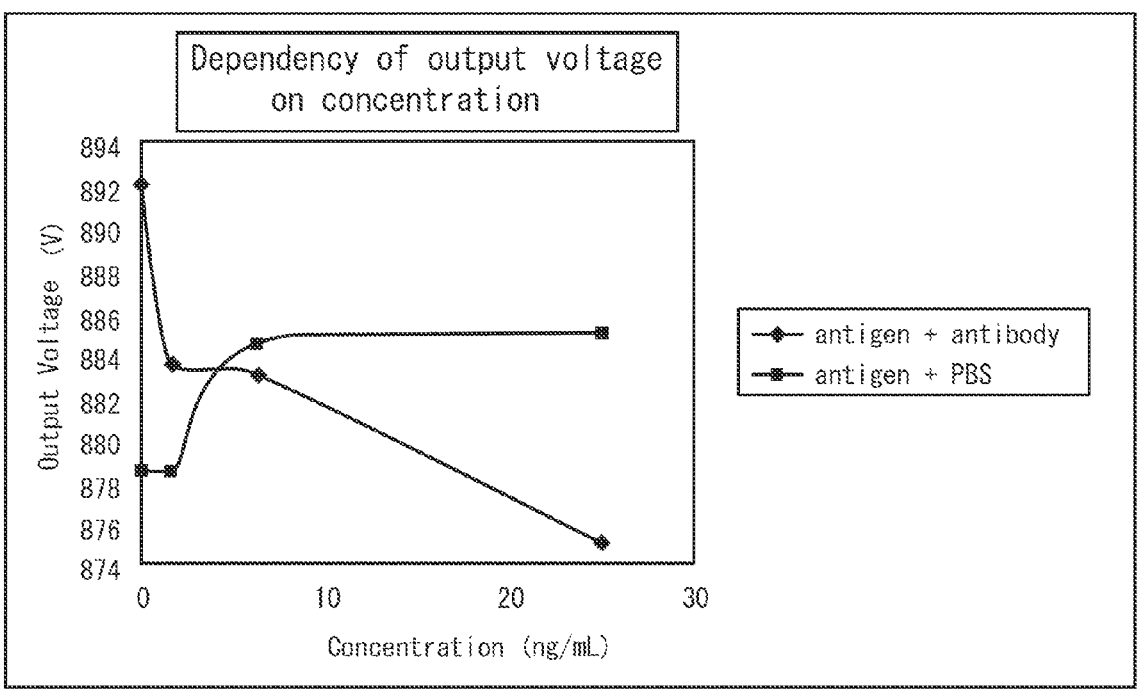
FIG. 19 is a chart showing the dependency of output voltage on antigen concentrations, in which ■ presents the reaction in the presence of an antibody, whereas ♦ presents the reaction in the absence of the antibody.

FIG. 19 is a chart presenting the results listed in Table 2, in which ■ represents the results of the system containing antigen only, whereas ♦ represents the results of the system containing both antigen and antibody. The system containing antigen only exhibited near-constant voltage characteristics, whereas the system containing both antigen and antibody exhibited decrease in output voltage with the increase in antigen concentrations. The electrical characteristics of the system containing both antigen and antibody are therefore considered to be dependent on antigen-antibody reactions.

In this example, the homogeneous method, wherein antibody is not attached to the insulator 3 of the sensor in advance, was adopted. However, the heterogeneous method, wherein antibody is attached to the insulator 3 of the sensor in advance, can also be adopted. In addition, DC measurement can also be conducted instead of AC measurement.

FIGS. 3 to 7 illustrate typical layouts of the reference electrode. Since the manufacturing procedures of the above sensor are the same as the procedures already described, description will be omitted.

FIG. 3 illustrates a structure wherein the reference electrode 6 was installed in addition to the work electrode 1 within the storage part 11. The potential difference between the work electrode 1 and the counter electrode 2 can be determined. However, if molecules attach to the electrodes and consequently the potential of each, the potential of the electrode on the substrate in particular, should deviate, true potential cannot be determined. If a reference electrode 6, which operates as an earth because its potential does not change, is used, the potential of both electrodes can be determined.

In addition, the reference electrode is also useful when observing the change in antigen-antibody reactions with time, and when a constant potential is given to the work electrode 1, the antigen starts reacting with the antibody on the surface, and the electric field on the surface changes. The wiring is the same as that shown in FIG. 8.

FIG. 4 illustrates a structure wherein a reference electrode 6 is installed outside the storage part 11.

The installation position of the reference electrode 1 in an electrochemical cell must be within the same cell where the work electrode 1 and counter electrode 2 are installed. In the structures shown in FIGS. 4, 5, 7, and 8, the role as a reference electrode cannot be satisfied in general electrochemical sense. Meanwhile, in the sensor, most of electric lines of force coming out of the work electrode 1 and reference electrode 6 on the substrate enter the substrate via an insulating film. In other words, the leak electric field of the work electrode 1 contributes to detection. Consequently, even if the reference electrode 6 is exposed, the potential difference between the counter electrode 2 and the reference electrode 6 remains the same, and by measuring the potential difference between the reference electrode 6 and the work electrode 1, the potential of the reference electrode 6 can be determined.

FIG. 5 illustrates the structure wherein the reference electrode 6 is embedded in the peripheral wall 4.

The reference electrode 6 in FIG. 5 works the same way as the reference electrode 6 in FIG. 4. Furthermore, since the reference electrode 6 in FIG. 5 is embedded in the peripheral wall 4, unlike the structure in FIG. 4 where the reference electrode 6 is exposed, the reference electrode 6 can be protected. When the reference electrode 6 is exposed, an arbitrary electrode, of the plurality of electrodes, can be used as the reference electrode 6 as shown in FIG. 16, but the reference electrode 6 may be contaminated due to the sample within the storage part 11 or dust. To prevent contamination and thus achieve stable potential measurement, the electrode specifically used as reference electrode 6 is embedded in the peripheral wall 4.

FIG. 6 illustrates the structure wherein the work electrode 1 and the reference electrode 6 are installed within the storage part, and the work electrode 1 and the reference electrode 6 are separated from each other with a partition wall, namely a salt bridge 7.

Materials to be tested are mostly proteins, and the charge status during antigen-antibody reactions is not regarded as a problem in general. From the experience of the inventor, however, materials to be tested having high ionicity, and thus easily electrifiable, such as calmodulin coordinating calcium, tend to achieve high sensitivity, but there is a possibility that they are being charged. To those samples, by controlling the ion concentrations using a salt bridge, stable reactions may be ensured. In the future, when detecting other items using one sample, by installing an ion-exchange membrane between reaction fields, crossover of the materials to be tested can be prevented to some extent.

In the case of calmodulin, using a calcium-ion exchange membrane is considered to be effective. Desirable exchange membranes must be provided depending on the materials to be tested. When detecting other items using the same specimen, or when the size of two or more materials to be tested varies, it will be possible to allow the materials to be tested to pass the salt bridge selectively, by adjusting the size and diameter of the salt bridge to the size of the material to be tested.

FIG. 7 illustrates the structure wherein the work electrode 1 and the reference electrode 6 are installed within the storage part 11, with the work electrode 1 and the reference electrode 6 separated from each other completely with the peripheral wall 4. In FIG. 7, the storage part 11 where the reference electrode 6 is installed stores antibody only, whereas the storage part where the work electrode 1 is installed stores the same amount of antibody, with the antigen of the material to be tested added to the antibody. This allows the amount of antigen and the change in dielectric constant of the solution with the advancement of antigen-antibody reactions to be determined based on the potential difference between the reference electrode and the work electrode.

| Reference Sign List | |
| --- | --- |
| 1: | Work electrode |
| 2: | Counter electrode |
| 3: | Insulator |
| 4, 4': | Peripheral wall |
| 5: | Sample solution |
| 6: | Reference electrode |
| 7: | Partition wall |
| 8A-8D: | Electrode pad |
| 9A-9C: | Bonding wire |
| 10: | Glass epoxy substrate |

-continued

| Reference Sign List | |
| --- | --- |
| 11: | Storage part |
| 12: | Pin-like electrode |
| 13: | Spring |
| 14: | Socket |
| 15: | Enclosure |
| 16: | Cover |
| 17: | Opening |
| 18: | Potentiostat |
| 21: | Work electrode |
| 22: | Counter electrode |
| 23: | Insulator |
| 24: | Peripheral wall |
| 25: | Sample solution |
| 100: | Sensor for detecting material to be tested |
| 110: | Package |
| 120: | Unit |
| 130: | Sensor for detecting material to be tested |
| R: | Reaction field |

What is claimed is:

1. A sensor for detecting a material to be tested, comprising:
   at least one work electrode; and
   a counter electrode integrated with the at least one work electrode via an insulator,
   wherein output voltage varies with the contact of the material with the at least one work electrode,
   characterized in that
   the at least one work electrode is formed smaller than the counter electrode and the insulator, and is provided to a part of the surface of the insulator, and that
   a peripheral wall for rising in a height direction perpendicular with the at least one work electrode is formed so as to cooperate with the at least one work electrode as a storage part for accommodating the material to be tested.

2. A sensor for detecting a material to be tested, comprising:
   at least one work electrode; and
   a counter electrode integrated with the at least one work electrode via an insulator,
   wherein a power supply is connected to the at least one work electrode and the counter electrode, and output voltage varies with the contact of the material with the at least one work electrode,
   characterized in that
   the counter electrode is formed in a shape of a plate,
   the insulator covers the upper face of the counter electrode,
   the at least one work electrode is provided on a part of the surface of the insulator,
   the contact area between the at least one work electrode and the insulator is smaller than the contact area between the counter electrode and the insulator, and
   a peripheral wall for rising in a height direction perpendicular with the at least one work electrode is formed so as to cooperate with the at least one work electrode as a storage part for accommodating the material to be tested.

3. A sensor for detecting material to be tested, comprising:
   a work electrode; and
   a counter electrode integrated with the work electrode via an insulator,
   wherein output voltage varies with the contact of the material with the work electrode,
   characterized in that
   the insulator is formed on a surface of the counter electrode, the work electrode is formed on an opposite surface of the insulator, a peripheral wall is provided on the work electrode, the peripheral wall has an opening for accommodating the material to be tested, the work electrode has an opening for exposing the surface of the insulator, and the material accommodated within the opening of the peripheral wall contacts the surface of the insulator via the opening of the work electrode.

4. The sensor for detecting material to be tested as set forth in any one of claims 1 to 3, characterized in that a reference electrode is provided on the surface of the insulator.

5. The sensor for detecting material to be tested as set forth in claim 4, characterized in that the reference electrode is placed outside the storage part.

6. The sensor for detecting material to be tested as set forth in claim 4, characterized in that the reference electrode is embedded in the peripheral wall.

7. The sensor for detecting material to be tested as set forth in claim 4, characterized in that the reference electrode is placed within the storage part.

8. The sensor for detecting material to be tested as set forth in claim 1, characterized in that the at least one work electrode is two or more work electrodes, and that the storage part is provided for each of the work electrodes.

9. The sensor for detecting material to be tested as set forth in claim 1, characterized in that the at least one work electrode is two or more work electrodes.

10. The sensor for detecting material to be tested as set forth in claim 1, characterized in that the storage part stores a given amount of the material to be tested to ensure stable operation of the at least one work electrode.

11. The sensor for detecting material to be tested as set forth in claim 1, characterized in that the peripheral wall constituting the storage part has water-repellent property.

12. The sensor for detecting material to be tested as set forth in claim 1, characterized in that the peripheral wall constituting the storage part has oil-repellent property.

* * * * *